United States Patent [19]

Mossman

[11] Patent Number: 5,221,798
[45] Date of Patent: Jun. 22, 1993

[54] CHANGING THE REGIOPURITY OF MIXTURES CONTAINING 4,4'-DISUBSTITUTED DIPHENYL CARBONATES

[75] Inventor: Allen B. Mossman, Wheaton, Ill.

[73] Assignee: Amoco Corporation, Chicago, Ill.

[21] Appl. No.: 437,102

[22] Filed: Nov. 16, 1989

Related U.S. Application Data

[62] Division of Ser. No. 292,403, Dec. 30, 1988.

[51] Int. Cl.$^5$ .............................................. C07C 69/96
[52] U.S. Cl. ..................................... 558/272; 558/274
[58] Field of Search ................................ 558/272, 274

[56] References Cited

U.S. PATENT DOCUMENTS

| | | | |
|---|---|---|---|
| 3,642,866 | 2/1972 | Witt et al. | 558/272 |
| 3,736,350 | 5/1973 | Mickel et al. | 558/272 |
| 4,101,569 | 7/1978 | Mazanek et al. | 558/272 |
| 4,182,726 | 1/1980 | Illuminate et al. | 558/274 |

Primary Examiner—José G. Dees
Assistant Examiner—Joseph M. Conrad, III
Attorney, Agent, or Firm—Thomas E. Nemo; Wallace L. Oliver; Frank J. Sroka

[57] ABSTRACT

The 4,2'-disubstituted diphenyl carbonate or, optionally, ether content of regioimpure mixtures of compounds of formula:

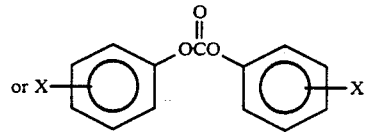

where X is F, Cl, and NO$_2$, can be decreased to essentially zero starting with o-, m- and p-containing regioimpure mixtures by treating with the corresponding m- or p-substituted phenol and, optionally, a decarboxylation catalyst and removing the o-substituted phenol produced by volatilization or recrystallization from a solvent.

7 Claims, No Drawings

CHANGING THE REGIOPURITY OF MIXTURES CONTAINING 4,4'-DISUBSTITUTED DIPHENYL CARBONATES

This is a division of application Ser. No. 292,403, filed Dec. 30, 1988.

BACKGROUND OF THE INVENTION

This invention relates to reducing the 4,2'-disubstituted diphenyl carbonate content of isomeric mixtures containing 4,4'-disubstituted diphenyl carbonate and, optionally, decarboxylating the product to the corresponding ether and, more particularly, to a process for decreasing the 4,2'-disubstituted diphenyl carbonate content of certain isomeric mixtures of the carbonate, wherein the phenyl groups are mono o-, m- and p-substituted, by treating the mixture with the corresponding m-or p-substituted phenol and, optionally, a decarboxylating agent, and removing the o-substituted phenol reaction product produced to form product carbonate, or optionally, ether. In particular, if a substituted diphenyl carbonate in which each phenyl ring is mono nitro-substituted is made by nitrating diphenyl carbonate, the product consists of a mixture of dinitrodiphenyl carbonate isomers in which each ring is mono nitro-substituted essentially in the ortho and para position. In such mixtures the 4,2'-dinitrodiphenyl carbonate content can be decreased to give an essentially pure, 4,4'-dinitrodiphenyl carbonate, or optionally ether, by treating the mixture with p-nitrophenol, and optionally, a decarboxylating agent, and removing the more volatile and more soluble o-nitrophenol reaction product by volatilization or recrystallization from a solvent.

The commercial preparation of substituted diphenyl compounds such as the diphenyl ethers in which each ring is monosubstituted has become important because of the use of such materials, in particular, the diamino derivatives, in polyamides, polyimides, and polyamide-imides. Because of the multiplicity of regioisomers formable in the manufacture of such compounds and the difference in properties of materials made from the different isomers, it is of commercial importance to be able to cheaply produce regiopure compounds. In particular, it is important to be able to make regiopure 4,4'-compounds such as 4,4'-dinitrodiphenyl ether which is easily reduced to the 4,4'-diaminodiphenyl ether for use in the polymer industry to manufacture polyamides, etc.

A number of methods have been reported to make 4,4'-diaminodiphenyl ether, none of which is entirely satisfactory. One procedure starts with the nitration of chlorobenzene to chloronitrobenzene which can be purified to give the para isomer essentially regiopure. That material is then reacted with regiopure p-nitrophenol to form regiopure 4,4'-dinitrodiphenyl ether which is then reduced to the diamine. This method is taught by J. A. Oscar in U.S. Pat. No. 3,387,041 issued to Dupont. Alternatively, diphenyl ether may be nitrated and the other isomers separated from the 4,4'-isomer in what is a costly and somewhat ineffective procedure; a method which is taught in French Patent No. 2,129,235 issued to Rhone Poulanc.

Now it has been found that by employing the lability of the diphenyl carbonate systems regiopure 4,4'-dinitrodiphenyl carbonate can be made by starting with a regioimpure mixture of nitrated diphenyl carbonates by treating the apparently mobile carbonate system in the melt or solution with 4-nitrophenol and removing the 2-nitrophenol produced by displacement either by volatilization or recrystallization. Inclusion of a decarboxylating agent in the process gives the 4,4'-disubstituted diphenyl ether instead of the carbonate.

BRIEF DESCRIPTION OF THE INVENTION

Described herein is a process to decrease the 4,2'-disubstituted diphenyl carbonate content of a regioimpure mixture of isomeric carbonates of formula:

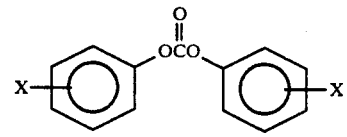

said mixture containing greater than about 50 weight percent of said 4,4'-disubstituted diphenyl carbonate and wherein X is a substituent selected from the group consisting of F, Cl, and $NO_2$ groups, which comprises heating said regioimpure mixture with the corresponding p-monosubstituted phenol in solution or in the melt and removing the corresponding o-substituted phenol produced by volatilization or recrystallization from a solvent.

Also described herein is a process to prepare regiopure 4,4'-dinitrodiphenyl ether from a regioimpure mixture comprising isomeric carbonate compounds of formula:

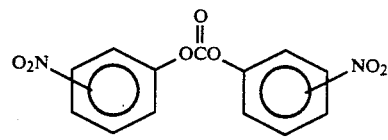

said regioimpure mixture containing greater than about 50 percent by weight of 4,4'-dinitrodiphenyl carbonate, which comprises heating said regioimpure mixture with p-nitrophenol in the presence of a decarboxylation catalyst and removing the o-nitrophenol produced by vaporization or recrystallization from a solvent.

In another aspect, the invention includes a process to decrease the 4,2'-dinitrodiphenyl carbonate content of a mixture containing 4,4'-, 4,3'- and 4,2'-dinitrodiphenyl carbonates which comprises heating said mixture with 3-nitrophenol in solution or in the melt and removing the 2-nitrophenol produced by volatilization or recrystallization from a solvent. In yet another aspect, a decarboxylation agent is added to the latter process in order to convert the mixture of carbonates to the corresponding isomeric ethers.

DETAILED DESCRIPTION OF THE INVENTION

The regioimpure mixture containing the 4,4'-disubstituted carbonate isomer may be obtained from any source and should contain greater than about 50 weight percent of the 4,4'-disubstituted isomer, preferably more than about 90 weight percent of the 4,4'-disubstituted isomer. For example, diphenyl carbonate which can be made by reacting phenol and phosgene can be nitrated with a sulfuric acid/nitric acid mixture to give a regioimpure mixture of dinitrophenyl carbonates in which each ring is monosubstituted. The 4,4'- and 4,2'-dinitrodiphenyl carbonates greatly predominate in the regioimpure mixture because of the regiodirecting influence of the carbonate group on each phenyl ring during nitration. Generally, such regioimpure mixtures contain greater than about 50 weight percent, more preferably greater than about 90 weight percent of 4,4'-dinitrodiphenyl carbonate isomer.

In order to reduce the amount of 4,2'-dinitrodiphenyl carbonate in the regioimpure mixture, advantage can be taken of the fact that diphenyl carbonates are a mobile (labile) system. If p-nitrophenol is mixed with the regioimpure mixture in a molar amount larger than the molar amount of 4,2'-dinitrodiphenyl carbonate present and the system heated or recrystallized from a solvent, o-nitrophenol is displaced by the p-nitrophenol. The o-nitrophenol can then be removed by volatilization or recrystallization from a solvent.

In the volatilization technique, about a five-fold mol excess or less, more preferably, about a three-fold mol excess or less, amount of p-nitrophenol is added to the regioimpure mixture of diphenyl carbonates and the mixture heated above about 100° C., more preferably, above about 130° C. for a sufficient time to remove the o-nitrophenol produced. Too high a temperature can result in unwanted thermal decomposition of the carbonate as can be understood by one skilled in the art. If desired, a decarboxylation agent can be added and simultaneous decarboxylation and removal of the o-nitrophenol accomplished to form the 4,4'-dinitrophenyl ether instead of the carbonate. As can be understood by one skilled in the art, the usual decarboxylation agents catalyze decomposition to the ether, but a decarboxylation catalyst based upon potassium carbonate is preferred. When the simultaneous decarboxylation method is used, heating temperatures are above about 100° C. and, more preferably, above about 200° C.

Alternatively, the replaced o-nitrophenol can be removed by recrystallization of the regioimpure carbonate mixture together with p-nitrophenol from an organic solvent such as benzene, toluene, hexane, etc., as can be understood by one skilled in the art. Molar ratios of p-nitrophenol to the amount of 4,2'-dinitrophenyl carbonate present are the same as are used in the volatilization procedure described above. The purified dinitrophenyl carbonate can then be converted to the corresponding ether by decarboxylation as described previously.

In another aspect of the invention, the amount of 4,3'-dinitrophenyl carbonate isomer which is generally produced in small amounts during the nitration of diphenyl carbonate can be augmented. If m-nitrophenol is added to the regioimpure mixture of nitrated diphenyl carbonates, it will displace o-nitrophenol similarly to the way p-nitrophenol does producing a deliberately regioimpure mixture of 4,4'-dinitrophenyl carbonate and 4,3'-dinitrophenyl carbonate which can be converted to the corresponding mixture of ethers if desired.

The following Examples will serve to illustrate certain specific embodiments of the herein disclosed invention. These Examples should not, however, be construed as limiting the scope of the novel invention contained herein as there are many variations which may be made thereon without departing from the spirit of the disclosed invention, as those of skill in the art will recognize.

EXAMPLES

EXAMPLE 1

Crude dinitrodiphenyl carbonate (15 g, 91.8% of 4,4'-dinitro isomer; 4.99% of 4,2'-dinitro isomer; and less than 1% of the 4,3'-isomer) was dissolved in toluene (30 ml). To this solution was added 4-nitrophenol (2.0 g). The hot solution was analyzed by gas-liquid chromatography and contained 82.42% dinitrodiphenyl carbonate (99.86% of 4,4'-dinitro isomer; 0.14% of 4,2'-dinitro isomer). The balance of the material is nitrophenols. The hot solution was chilled overnight and the resulting solid collected by filtration, dried and weighed. The resulting material (15.44 g) was analyzed by GLC and found to contain the desired carbonate isomer (90.4% of 4,4'-dinitro isomer; trace of 4,2'-dinitro isomer) and nitrophenols (7.49% of the 4-isomer; and 2.11% of 2-isomer).

EXAMPLE 2

Diphenyl carbonate (107.2 g, 0.5 mol) was nitrated with a mixture of nitric and sulfuric acids. Ethyl acetate was added to the reaction mixture after the reaction had been quenched with ice. The organic layer was dried and 4-nitrophenol (10.0 g) was added to the solution. This solution was concentrated and the resulting solid dried in a vacuum oven 80° C. overnight. The resulting crude product was washed with hexane and dried again resulting in crude dinitrodiphenyl carbonate (179.5 g) containing isomeric carbonates in the ratio 93.4%:6.6%, 4,4'-dinitro isomer to 4,2'-dinitro isomer. This crude mixture of carbonates was taken up in toluene (400 ml) and 4-nitrophenol (5.0 g) was added. Hexane (150 ml) was added, and the solution allowed to cool and crystallize. The resulting solid was dried and analyzed by GLC. The results of this analysis indicated that the solid (127.96 g) was 99.98% of the 4,4'-dinitrodiphenyl carbonate which is an 83.6% yield based upon the starting amount of diphenyl carbonate.

EXAMPLE 3

A solution was prepared containing crude 4,4'-dinitrodiphenyl carbonate (96.6% of 4,4'-dinitro isomer; trace, 4,3'-dinitro isomer; and 3.4% of 4,2'-dinitro isomer), in toluene (300 ml). To this solution was added 4-nitrophenol (6.0 g) and the hot solution stirred for 5 min. The hot solution was filtered to remove any undissolved impurities, and cooled slowly to room temperature. After sitting for some time at room temperature the solution was chilled in a refrigerator for 6 hr, and the resulting crystals filtered. After drying the yellow solid (87 g, 98.95% of 4,4'-dinitro isomer, 0.7% of 4,3'-dinitro isomer, and 0.4% of 4,2'-dinitro isomer) was slurried in hexane (400 ml) and stirred for 2 hr. The solid was filtered and the resulting material (78.7 g) contained only traces of the isomeric carbonate. The majority impurity in the resulting solid was 4-nitrophenol.

EXAMPLE 4

A solution of crude dinitrodiphenyl carbonate (73% of 4,4'-dinitro isomer; 4% of 4,2'-dinitro isomer; and 1.5% of 4,3'-dinitrodiphenyl carbonate and 2.4% of 4-isomer; 11.1% of 2-isomer; and 4.4% of 3-nitrophenol) was placed in a 100 ml round bottom flask. This flask was placed on a kugelrohr and heated at 175° C. and 100 torr for 2.5 hr. Following this the material remaining in the flask had the following composition when analyzed by GLC.

Carbonates: 4,4'-dinitro isomer, 71.4%; 4,2'-dinitro isomer, trace; 4,3'-dinitro isomer, trace.

Phenols: 4-nitro isomer, 12.3%; 2-nitro isomer, 6.5%; and 3-nitro isomer, 3.4%.

Ethers: 4,4'-dinitro isomer, 1.6%.

EXAMPLE 5

A solution of crude dinitrodiphenyl carbonate (5.0 g, 73% of 4,4'-dinitro isomer; 4% of 4,2'-dinitro isomer; and 1.5% of 4,3'-dinitrodiphenyl carbonate and 2.4% of 4-; 11.1% of 2-; and 4.4% of 3-nitrophenol) was placed on a 100 cc round bottom flask. A small amount of 4-nitrophenol (120 mg) was added to the flask. This flask was placed on a kugelrohr and heated at 250° C. and 100 torr for 1 hour. Following this the material remaining in the flask had the following composition when analyzed by GLC.

Carbonates: 4,4'-dinitro isomer, 6.8%; and 4,2'-dinitro isomer, 0.5%.

Phenols: 4-nitro isomer, 17.3%; 2-nitro isomer; and 3-nitro isomer, 0.8%.

Ethers: 4,4'-dinitro isomer, 73.1%; and 4,2' dinitro isomer, 0.6%.

EXAMPLE 6

A solution of crude dinitrodiphenyl carbonate (5.0 g, 73% of 4,4'-dinitro isomer; 4% of 4,2'-dinitro isomer; 1.5% of 4,3'-dinitrodiphenyl carbonate; and 2.4% of 4-; 11.1% of 2-; and 4.4% of 3-nitrophenol) was placed in a 100 ml round bottom flask. A small amount of 4-nitrophenol (100 mg) was added to the flask. This flask was placed on a kugelrohr and heated at 275° C. and 100 torr for 0.5 hours. Following this the material remaining in the flask had the following composition when analyzed by GLC.

Carbonates: 4,4'-dinitro isomer, 1.9%; and 4,2'-dinitro isomer, 0.8.

Phenols: 4-nitro isomer, 21.4%; 2-nitro isomer, trace; and 3-nitro isomer, 0.8%.

Ethers: 4,4'-dinitro isomer, 74.5%; and 4,2'-dinitro isomer, 0.6%.

EXAMPLE 7

Diphenyl carbonate (10.71 g, 0.05 mol) was nitrated in the presence of trifluoromethanesulfonic acid (50 g) and dichloromethane (200 ml). After the reaction had been quenched with ice, the organic layer was separated, washed with water and saturated bicarbonate solution, and dried over sodium sulfate. Analysis of this solution indicated a relatively poor selectivity in the nitration (76.9% of 4,4'-dinitro isomer and 23.1% of 4.2'-dinitro isomer). The dried solution was concentrated by rotatory evaporation to a solid (16.0 g). To this solid 4-nitrophenol (4.0 g) was added. This mixture was placed on a kugelrohr and heated at 275° C. at 100 torr for 35 minutes. At this time the mass of material in the flask was 11.95 g and contained 2-nitrophenol, 1.3%, 4-nitrophenol, 17.0%, 4,4'-dinitrodiphenyl ether, 1.65%, 4,2'-dinitrodiphenyl carbonate, 0.65%, and 4,4'-dinitrodiphenyl carbonate, 79.5%.

Potassium carbonate (100 mg) was added to the flask and the reaction returned to the kugelrohr for an additional period (200° C., 100 torr, 30 min). Following this additional pyrolysis the reaction was cooled and removed from the kugelrohr. GLC analysis of the material remaining in the flask indicated the presence of only 4,4'-dinitrodiphenyl ether (84.2%) and 4-nitrophenol (15.8%). This material was taken up in ethyl acetate, washed with sodium hydroxide, dried and concentrated to a crude dinitrodiphenyl ether (8.05 g, 61.5%) containing 98% of the desired ether and 2% of 4-nitrophenol.

EXAMPLE 8

A sample of purified 4,4'-dinitrodiphenyl carbonate (10 g; 94% 4,4'-dinitro isomer) was placed in a 250 ml round bottom flask. To this was added 4-nitrophenol (100 mg) and potassium carbonate (100 mg of powder). The flask was heated in a kugelrohr under 20 in of mercury pressure at 200° C. for one hr. The material remaining weighed 8.75 g. The solid was dissolved in methylene chloride, filtered, giving a solid residue (0.75 g). A solution of 8.00 g of crude product was analyzed by GLC and found to contain 94.9% of 4,4'-dinitrodiphenyl ether, trace of 4,3'-dinitrodiphenyl ether, 0.2% of 4,2'-dinitrodiphenyl ether, 2.8% of 4-nitrophenol, and 2.1% of 4,4'-dinitrodiphenyl carbonate.

What is claimed is:

1. A process to decrease the 4,2'-disubstituted diphenyl carbonate content of a mixture of isomeric carbonates of formula:

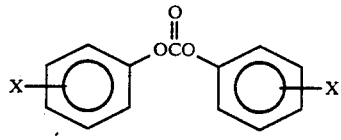

said mixture containing greater than about 50 weight percent of said 4,4'-disubstituted diphenyl carbonate and wherein X is a substituent selected from the group consisting of F, Cl, and NO$_2$ groups, which comprises heating said mixture with the corresponding p-substituted phenol in solution or in the melt and removing the corresponding o-substituted phenol produced by volatilization or recrystallization from a solvent.

2. The process of claim 1 wherein X is NO$_2$.

3. The process of claim 2 wherein said o-substituted phenol is removed by volatilization.

4. The process of claim 2 wherein said o-substituted phenol is removed by recrystallization from a solvent.

5. The process of claim 3 wherein said mixture contains greater than about 90 weight percent of said 4,4'-disubstituted diphenyl carbonate.

6. The process of claim 4 wherein said mixture contains greater than about 90 weight percent of said 4,4'-disubstituted diphenyl carbonate.

7. A process to decrease the 4,2'-dinitrodiphenyl carbonate content of a mixture containing 4,4'-, 4,3'- and 4,2'-dinitrodiphenyl carbonates which comprises heating said mixture with 3-nitrophenol in solution or in the melt and removing the 2-nitrophenol produced by volatilization or recrystallization from a solvent.

* * * * *